(12) United States Patent
Smith

(10) Patent No.: US 10,799,718 B2
(45) Date of Patent: Oct. 13, 2020

(54) COMPUTER SYSTEM INTEGRATION

(71) Applicant: Elekta Limited, Sussex (GB)

(72) Inventor: Adrian Maxwell Smith, London (GB)

(73) Assignee: ELEKTA LIMITED, Sussex (GB)

( * ) Notice: Subject to any disclaimer, the term of this patent is extended or adjusted under 35 U.S.C. 154(b) by 463 days.

(21) Appl. No.: 15/053,973

(22) Filed: Feb. 25, 2016

(65) Prior Publication Data
US 2016/0243380 A1    Aug. 25, 2016

(30) Foreign Application Priority Data

Feb. 25, 2015    (GB) .................................. 1503170.1

(51) Int. Cl.
| | |
|---|---|
| G06F 3/048 | (2013.01) |
| A61N 5/10 | (2006.01) |
| G06F 9/451 | (2018.01) |
| G06F 9/54 | (2006.01) |
| G06F 3/0481 | (2013.01) |
| G06F 3/0484 | (2013.01) |
| G06F 3/14 | (2006.01) |
| G09G 5/12 | (2006.01) |
| G09G 5/14 | (2006.01) |
| H04N 7/18 | (2006.01) |

(52) U.S. Cl.
CPC ......... *A61N 5/1048* (2013.01); *G06F 3/0481* (2013.01); *G06F 3/04845* (2013.01); *G06F 3/1454* (2013.01); *G06F 9/452* (2018.02); *G06F 9/542* (2013.01); *G09G 5/12* (2013.01); *G09G 5/14* (2013.01); *H04N 7/18* (2013.01); *A61N 2005/1059* (2013.01); *A61N 2005/1074* (2013.01); *G06F 2209/545* (2013.01); *G09G 2380/08* (2013.01)

(58) Field of Classification Search
None
See application file for complete search history.

(56) References Cited

U.S. PATENT DOCUMENTS

| | | | | |
|---|---|---|---|---|
| 6,928,490 B1 * | 8/2005 | Bucholz | ................ | G06F 19/327 340/12.32 |
| 8,943,373 B1 | 1/2015 | Angaluri et al. | | |
| 2001/0055281 A1 * | 12/2001 | Kwan | ................... | G06F 9/4887 370/280 |

(Continued)

OTHER PUBLICATIONS

European Search Report issued in European Patent Application No. 15188432.7-1957, dated Jun. 23, 2016, 8 pages.

(Continued)

*Primary Examiner* — William C Trapanese
(74) *Attorney, Agent, or Firm* — Finnegan, Henderson, Farabow, Garrett & Dunner LLP

(57) ABSTRACT

A system and method of integrating a first computer and a second computer is disclosed. The first computer executes a software application having a graphical user interface. The second computer renders the graphical user interface, receives an identification of an event that has occurred in the software application, and identifies an action to be performed by the second computer in response to the occurrence of the event, the action being identified from a predefined sequence of actions. The second computer performs the identified action to modify the rendering of the graphical user interface.

20 Claims, 4 Drawing Sheets

| Current State | Received Event | Action(s) | Next State | |
|---|---|---|---|---|
| 0 | | Render application 135 in Area 202<br>Render application 115 in Area 204<br>Render application 145 in Area 206 | 1 | 119 |
| 1 | "Login Successful" event from application 135 on third computer 130 | Terminate rendering application 135<br>Render application 125 in Area 202 | 2 | |
| 2 | "Select State 3" event from application 125 on first computer 120 | Move application 115 to Area 202<br>Move application 125 to Area 204 | 3 | |
| 2 | "Terminate" event from application 125 on first computer 120 | Terminate rendering all applications | - | |
| 3 | "Select State 2" event from application 115 on second computer 110 | Move application 125 to Area 202<br>Move application 115 to Area 204 | 2 | |
| 3 | "Warning" event from application 145 on third computer 130 | Grant keyboard focus to application 145 | 3 | |
| 3 | "Terminate" event from application 125 on first computer 120 | Terminate rendering all applications | - | |

(56) References Cited

U.S. PATENT DOCUMENTS

| | | | |
|---|---|---|---|
| 2006/0063999 A1* | 3/2006 | Herron | A61N 5/1049 600/407 |
| 2006/0230156 A1 | 10/2006 | Shappir et al. | |
| 2006/0274885 A1* | 12/2006 | Wang | A61N 5/103 378/65 |
| 2007/0041496 A1* | 2/2007 | Olivera | A61N 5/103 378/65 |
| 2009/0070404 A1 | 3/2009 | Mazzaferri | |
| 2010/0049890 A1 | 2/2010 | Best et al. | |
| 2011/0219331 A1* | 9/2011 | DeLuca | G06F 3/048 715/799 |
| 2012/0011296 A1 | 1/2012 | Ke | |
| 2012/0095778 A1* | 4/2012 | Gross | G16H 40/63 705/2 |
| 2012/0226771 A1* | 9/2012 | Harrington | G06F 19/3418 709/217 |
| 2013/0139103 A1 | 5/2013 | Laborczfalvi et al. | |
| 2013/0283181 A1 | 10/2013 | Mazzaferri | |
| 2014/0304355 A1* | 10/2014 | Kamath | H04L 67/2842 709/213 |

OTHER PUBLICATIONS

International Search Report for GB Application No. 1503170.1, filed Feb. 25, 2015 (dated Jul. 30, 2015).

* cited by examiner

| Current State | Received Event | Action(s) | Next State |
|---|---|---|---|
| 0 | | Render application 135 in Area 202<br>Render application 115 in Area 204<br>Render application 145 in Area 206 | 1 |
| 1 | "Login Successful" event from application 135 on third computer 130 | Terminate rendering application 135<br>Render application 125 in Area 202 | 2 |
| 2 | "Select State 3" event from application 125 on first computer 120 | Move application 115 to Area 202<br>Move application 125 to Area 204 | 3 |
| 2 | "Terminate" event from application 125 on first computer 120 | Terminate rendering all applications | - |
| 3 | "Select State 2" event from application 115 on second computer 110 | Move application 125 to Area 202<br>Move application 115 to Area 204 | 2 |
| 3 | "Warning" event from application 145 on third computer 130 | Grant keyboard focus to application 145 | 3 |
| 3 | "Terminate" event from application 125 on first computer 120 | Terminate rendering all applications | - |

Fig. 3

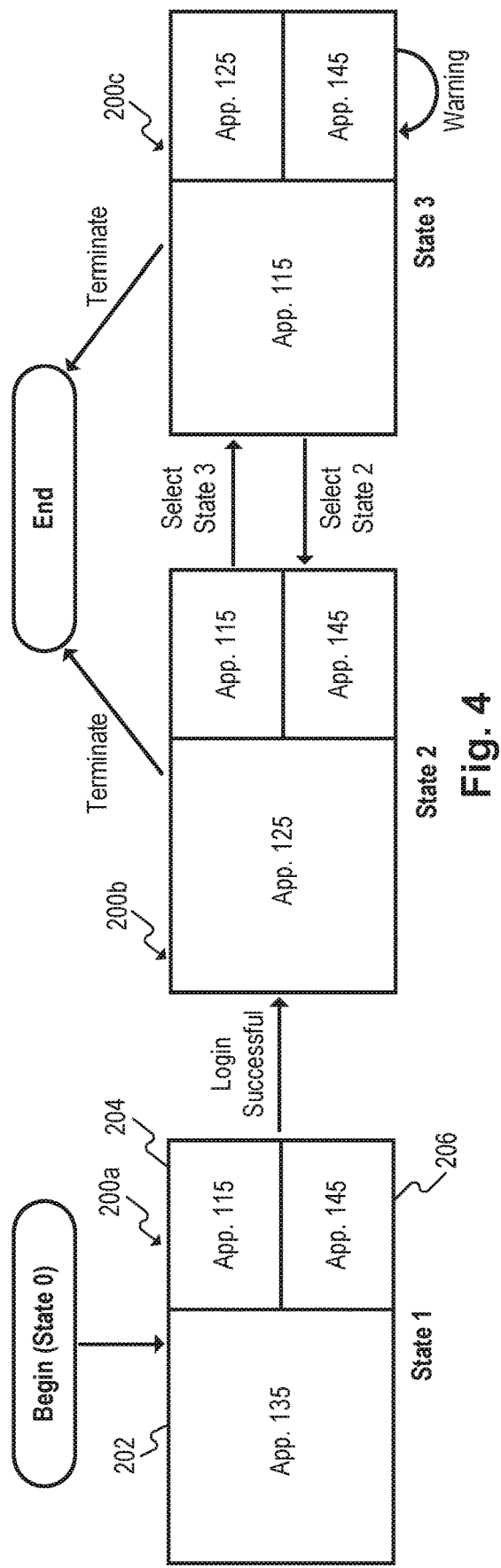

Fig. 4

COMPUTER SYSTEM INTEGRATION

CROSS REFERENCE TO RELATED APPLICATION

This application is based upon and claims the benefit of prior United Kingdom Patent Application No. 1503170.1, filed on Feb. 25, 2015, the entire contents of which are incorporated herein by reference.

TECHNICAL FIELD

The present disclosure relates to computer systems. More specifically, the present disclosure relates to a method and apparatus for integrating software applications being executed by a plurality of computers into a single computer.

BACKGROUND OF THE DISCLOSURE

Some computing tasks involve the use of several different software applications, each of which is executed by a different computer. In order to accomplish the computing task successfully, a user may have to interact with each of the software applications on each of the computers. For example, each of a plurality of computers may be connected to a respective item of hardware that is needed to accomplish a particular portion of the computing task, and dedicated software applications may be needed to control or receive data from each item of hardware. In this example, the use of multiple different items of hardware may mean that it is difficult or undesirable to replace the plurality of computers with a single computer. As another example, the computing task may call for actions to be performed by software applications that require different operating systems. In this example, the need for multiple different operating systems may mean that it is difficult or undesirable to execute all of the software applications by a single computer.

A number of practical difficulties arise from using multiple computers to accomplish a particular computing task. For example, it is inconvenient for a user to move from one computer to another in order to perform different portions of the task. Furthermore, having a different keyboard, monitor and mouse for each computer is costly and consumes space.

A possible solution to these practical difficulties might be to couple multiple computers to a single keyboard, monitor and mouse using a KVM (keyboard, video and mouse) switch. However, this would not be a good solution to the practical difficulties because it is onerous for the user to select the correct computer to perform each portion of the task via the KVM switch. Furthermore, the use of a KVM switch has the disadvantage that the user cannot see events that occur on computers that are not connected to the monitor via the KVM switch at a particular moment in time. Yet further, it can be costly to install keyboard, video and mouse cables between each computer and the KVM switch.

Another possible solution to these practical difficulties might be to use a software-implemented equivalent of a KVM switch, such as Multiplicity™ by EdgeRunner LLC. Such software-implemented KVM switches communicate keyboard, video and mouse data over a communications network, thus avoiding the need to install keyboard, video and mouse cables between each computer and the computer hosting the software-implemented KVM switch. However, software-implemented KVM switches still require the user to select the correct computer to perform each portion of the task, and still have the disadvantage that the user cannot see events that occur on computers that are not selected at a particular moment in time.

Thus, there is a need for an improved way of integrating software applications being executed by a plurality of computers into a single computer, which overcomes or mitigates some of the previously-mentioned practical difficulties.

SUMMARY

A first aspect provides a method of integrating a first computer and a second computer, the first computer executing a first software application having a first graphical user interface, the method being performed at the second computer and comprising: rendering the first graphical user interface; receiving an identification of an event that has occurred in the first software application; identifying an action to be performed by the second computer in response to the occurrence of the event, wherein the action is identified from a predefined sequence of actions; and performing the identified action to modify the rendering of the first graphical user interface.

Identifying an action may comprise identifying a current state of the second computer; and consulting a look-up table to identify a predefined action associated with the current state of the second computer and the event that has occurred.

The method may further comprise establishing, by a remote presentation program executed by the second computer, a remote presentation protocol session between the first computer and the second computer; and using the remote presentation protocol session to communicate information pertaining to the first graphical user interface between the first computer and second computer via a network, wherein the first graphical user interface is rendered using the remote presentation program. The method may further comprise establishing a communication channel between the first computer and the second computer, the communication channel being distinct from the remote presentation protocol session, wherein the identification of an event is received at the second computer via the communication channel.

The second computer may execute a second software application having a second graphical user interface, and the method may further comprise rendering the first graphical user interface and the second graphical user interface simultaneously by the second computer. Performing the identified action may further cause the second computer to modify the rendering of the second graphical user interface. The method may further comprise receiving an identification of a second event, the second event having occurred in the second software application; identifying a second action to be performed by the second computer in response to the occurrence of the second event, wherein the second action is identified from the predefined sequence of actions; and performing the identified second action to modify the rendering of the first graphical user interface and/or the second graphical user interface.

The method may further comprise integrating a third computer with the first and second computers, the third computer executing a third software application having a third graphical user interface, by rendering the first graphical user interface and the third graphical user interface simultaneously by the second computer. Performing the identified action may further cause the second computer to modify the rendering of the third graphical user interface. The method may further comprise receiving an identification of a third event, the third event having occurred in the third software application; identifying a third action to be performed by the second computer in response to the occurrence of the third event, wherein the third action is identified from the predefined sequence of actions; and performing the identified third action to modify the rendering of the first graphical user interface and/or the third graphical user interface.

Performing one of said identified actions to modify the rendering of any of the first, second or third graphical user interfaces may comprise causing the second computer to modify the behaviour and/or appearance of that graphical user interface. Performing one of said identified actions may cause the second computer to perform any one or more of: changing the position at which any of the first, second or third graphical user interfaces is displayed; or changing the size at which any of the first, second or third graphical user interfaces is displayed; or terminating rendering any of the first, second or third graphical user interfaces; or granting focus of an input device to any of the first, second or third graphical user interfaces, wherein the input device is communicatively coupled to the second computer.

The method may further comprise generating a message at the first computer, the message identifying the event that has occurred in the first software application; and transmitting the message, by the first computer, to the second computer.

A further aspect provides a processor-readable medium comprising instructions which, when executed by a processor, cause the processor to perform a method as described herein.

A further aspect provides an apparatus for performing a method as described herein. The apparatus may comprise a processor and a memory coupled to said processor, the memory comprising instructions that when executed cause the processor to perform a method as described herein.

A further aspect provides a radiotherapy system comprising: a computer operable to communicate with a further computer, the further computer being connected to a device for generating radiation, the further computer comprising a treatment control program for controlling the device for generating radiation, the treatment control program having a graphical user interface, wherein the computer is configured to: render the graphical user interface; receive an identification of an event that has occurred in the treatment program; identifying an action to be performed by the computer in response to the occurrence of the event, wherein the action is identified from a predefined sequence of actions; and performing the identified action to modify the rendering of the graphical user interface. The computer may be further operable to communicate with a third computer, the third computer comprising an oncology information program for providing information relating to a patient to be treated by the radiotherapy system.

BRIEF DESCRIPTION OF THE DRAWINGS

Embodiments will now be described, purely by way of example, with reference to the accompanying drawings, wherein like elements are indicated using like reference signs, and in which:

FIG. 3 is an example of an event table;

FIG. 4 is an example of a sequence of screens generated by the event table shown in FIG. 3.

DETAILED DESCRIPTION

Figure 1:
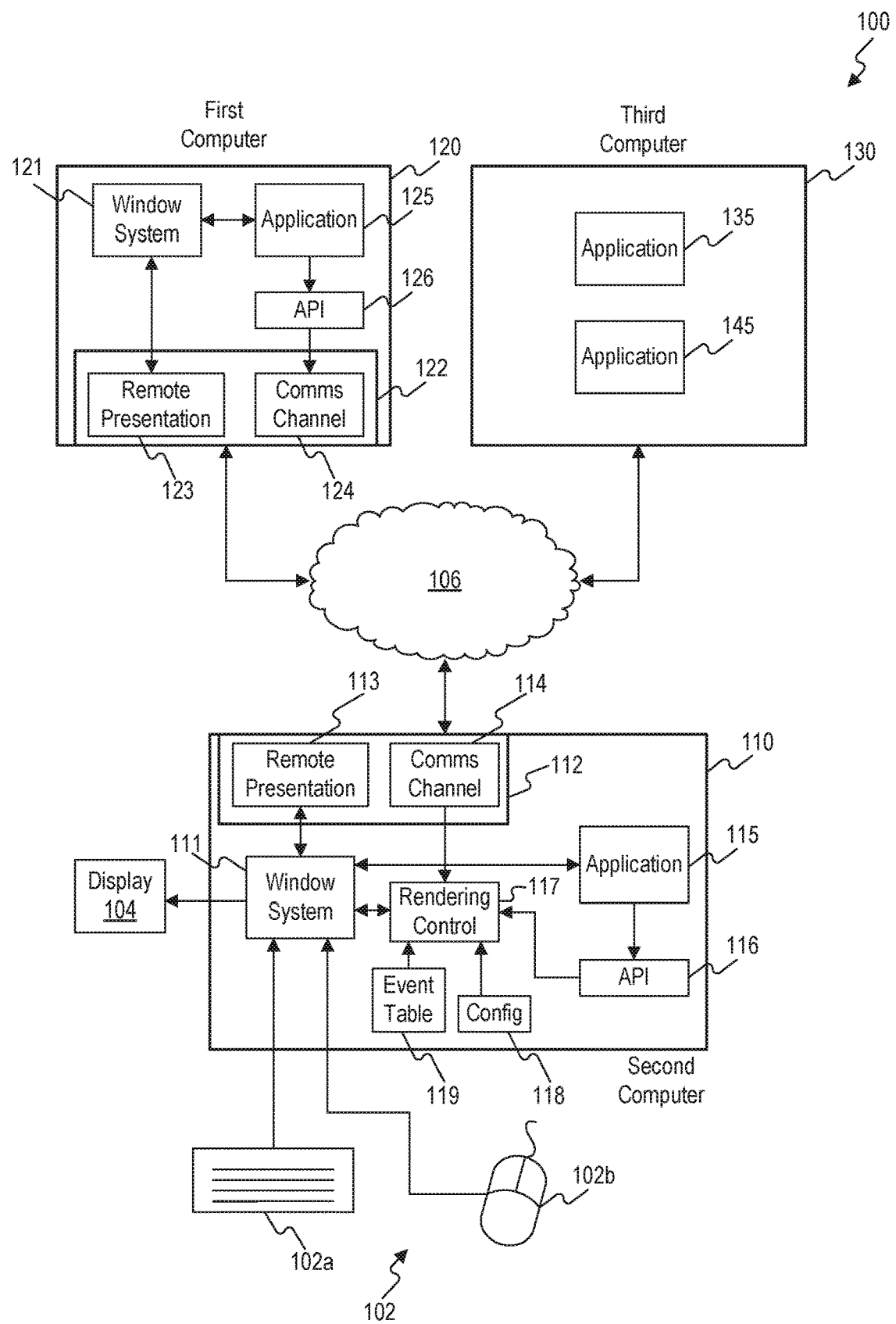
FIG. 1 is a schematic diagram of a computer system.

FIG. 1 is a schematic diagram of a networked computer system 100. The computer system 100 comprises a first computer 120 and a second computer 110. The computer system 100 may optionally comprise any number of further computers, such as a third computer 130. Any of the computers 110, 120, 130 can be a real computer or a virtual machine. For the sake of simplicity, the following description of the computer system 100 assumes that all of the computers 110, 120, 130 are real computers.

The computers 110, 120, 130 are linked to each other by a communications network 106, such that the computers can communicate via the network 106. The network 106 may comprise any suitable wired or wireless communication technology, or any combination of different wired and/or wireless communication technologies. For example, the network 106 may comprise a short-range wireless communication link, such as a Bluetooth™ or IEEE 802.11 (WiFi™) link. As another example, the network 106 may comprise a local area network (LAN), such as a wired network based upon Ethernet communication technologies. As yet another example, the network 106 may comprise a wide area network (WAN), such as the Internet or a cellular telephone network.

The first computer 120 comprises a processor and memory (not shown in FIG. 1). The processor of the first computer 120 executes various programs that are stored in the memory, including a window system 121, communication software 122, and one or more software applications 125.

The second computer 110 comprises a processor and memory (not shown in FIG. 1). The processor of the second computer 110 executes various programs that are stored in the memory, including a window system 111, communication software 112 and a rendering control program 117. The processor of the second computer 110 may optionally execute one or more software applications 115. The memory of the second computer 110 also stores configuration information 118 and an event table 119. One or more input devices 102, such as a keyboard 102a and/or a mouse 102b, are connected to the second computer 110. A display device 104, such as a monitor, is connected to the second computer 110. Any suitable type of input device 102 or display device 104 may be used. A combined input device and display device, such as a touchscreen, may also be used. The input devices 102 and display device 104 can be connected to the second computer 110 by a wired or wireless connection.

The first computer 120 need not be directly connected to an input device because, as will be explained below, input can be provided to the first computer via the input devices 102 that are connected to the second computer 110. Similarly, the first computer 120 need not be directly connected to a display device because it can provide its output to the display device 104 that is connected to the second computer 110.

The third computer 130 comprises a processor and memory (not shown in FIG. 1). The processor of the third computer 130 executes various programs that are stored in the memory, including one or more software applications 135, 145. The third computer 130 is similar to the first computer 120 and, therefore, need not be described in detail. Similarly, if the computer system 100 comprises any further computers (not shown in FIG. 1), these can also be considered to be similar to the first computer 120 and need not be described in detail. For the sake of clarity, only the first computer 120 is discussed in the following description of the functionality of the computer system 100. However, it will be appreciated that references to the first computer 120 could be replaced and/or supplemented by references to the third computer 130 or further computers, where appropriate.

A window system 111, 121 is a program, or a suite of programs, that allows a computer 110, 120 to provide a graphical user interface (GUI). For example, the window system 111, 121 can allow a software application 115, 125 to present its output in a window on a display device 104. The window system 111, 121 can also allow a software application 115, 125 to receive an input from an input device 102. Any suitable window system 111, 121 may be used. For example, the window system 111, 121 may be integrated with an operating system (e.g. Microsoft Windows™) that is executed by a computer 110, 120. Alternatively, the window system 111, 121 may be separate from the operating system (e.g. the X Window System™, which is executed by UNIX™-like operating systems). The window systems 111, 121 that are executed by each computer 110, 120 need not be the same.

The software applications 115, 125 can be any type of program that has a graphical user interface. The software applications 115, 125 typically use a respective window system 111, 121 to provide their GUIs. For example, the software applications 115, 125 can instruct a window system 111, 121 to display one or more windows in which to present a visual output and/or may be notified by the window system when a user interacts with the one or more windows using an input device 102. However, the software applications need not necessarily use a window system 111, 121. For example, the software applications 115, 125 could be legacy programs, such as programs written for MS-DOS™, that can provide a graphical user interface without a window system 111, 121. The scope of the claims encompasses software applications 115, 125 having any functionality. In certain examples, the software applications 115, 125 have an interrelated functionality, such that the rendering control program 117 can integrate the software applications 115, 125 in order to accomplish a particular task.

The communication software 112, 122 allows the computers 110, 120 to communicate with each other via the network 106. The communication software 112, 122 includes remote presentation programs 113, 123. A remote presentation program 113, 123 allows the graphical user interface of a software application 125 being executed by the first computer 120 to be displayed on the second computer 110. To achieve this, respective remote presentation programs 113, 123 being executed by both computers 110, 120 exchange information pertaining to the graphical user interface via the network 106. The remote presentation programs 113, 123 typically allow information that describes the appearance of the graphical user interface to be transmitted from the first computer 120 to the second computer 110, such that the graphical user interface can be rendered by the second computer 110. The remote presentation programs 113, 123 also typically allow information that describes a user input to the graphical user interface to be transmitted from the second computer 110 to the first computer 120, such that a user of the second computer 110 can interact with the software application 125. The user input may include input from any suitable input device, such as a keyboard 102a and/or a mouse 102b. The information pertaining to the graphical user interface is communicated via the network 106 using a remote presentation protocol. In one example of the computer system 100, the remote presentation protocol is Remote Desktop Protocol (RDP), provided by Microsoft Corporation. In this example, the remote presentation program 123 executed by the first computer 120 is an RDP server, and the remote presentation program 113 executed by the second computer 110 is an RDP client. The RDP client 113 establishes an RDP session with the RDP server 123, so as to allow information pertaining to the graphical user interface to be exchanged via the network 106. Any other suitable remote presentation protocols and remote presentation programs may be used. For example, the remote presentation protocol may be Remote Framebuffer Protocol (RFP), and the remote presentation programs 113, 123 may be Virtual Network Computing (VNC) applications. The claims are not intended to be limited to any particular remote presentation protocol or remote presentation program.

The communication software 112, 122 also includes communication channel components 114, 124 for establishing a communication channel between the second computer 110 and the first computer 120. The communication channel allows the first computer 120 to provide information relating to the occurrence of an event in a software application 125 being executed by the first computer 120 to the second computer 110. The term "event" as used herein describes an occurrence or happening that is significant to a program. In one example, the communication channel is a Transmission Control Protocol (TCP) socket connection. In this example, the second computer 110 comprises a TCP server 114, and the first computer 120 comprises a TCP client 124. The TCP server 114 receives messages, via the network 106, that are addressed to a predefined TCP port of the second computer 110. The TCP server 114 directs such messages to the rendering control program 117. Thus, in order for the first computer 120 to notify the second computer 110 of the occurrence of an event, the TCP client 124 sends a message, via the network 106, to the predefined TCP port of the second computer 110. Any other suitable method of communicating the occurrence of events from the first computer 120 to the second computer 110 may be used. For example, the communication channel can be an RDP virtual channel, such that the remote presentation programs 113, 123 are integrated with the communication channel components 114, 124 for establishing a communication channel. The claims are not intended to be limited to any particular type of technology for establishing a communication channel between the second computer 110 and the first computer 120.

The first computer 120 may comprise an application programming interface (API) 126 to facilitate the provision of information relating to the occurrence of an event in a software application 125 to the second computer 110. The API 126 comprises one or more procedures, functions or methods (hereinafter referred to as "API calls") that can be invoked or executed by the software application 125. When the software application 125 invokes an API call, the API 126 causes a message to be sent via the network 106 to the second computer 110, using the communication channel.

The second computer 110 may also comprise an application programming interface 116 to facilitate the provision of information relating to the occurrence of an event in a software application 115 executed by the second computer 110 to the rendering control program 117. The API 116 of the second computer 110 has similar functionality to the API 126 of the first computer 120. However, as the software application 115 and the rendering control program 117 are both executed by the second computer 110, the API 116 does not cause messages to be sent via the network 106. Instead, when the software application 115 invokes an API call, the API 116 causes a message to be sent directly to the rendering control program 117. The API 116 can send a message to the rendering control program 117 using any suitable method of inter-process communication.

Some examples of the API calls provided by the APIs 116, 126 will now be described. One API call notifies the second computer 110 of the occurrence of an event within a software application 115, 125. This API call has the form SendEvent (Destination, Source, EventName). Destination identifies the second computer 110, and may be the network name or the Internet Protocol (IP) address of the second computer 110. Source identifies the software application 115, 125 within which the event occurred. EventName identifies the particular event that occurred in the software application 115, 125. Thus, invocation of the SendEvent API call causes the second computer 110 to receive a message that identifies an event and the software application 115, 125 in which it occurred. Another API call causes the second computer 110 to display text selected by the software application 115, 125. This API call has the form SendDisplayText (Destination, Source, Text). The Destination and Source parameters have the same meaning as discussed in connection with the SendEvent API call, while Text is a character string. Invocation of the SendDisplayText API call causes the second computer 110 to receive a message that identifies a character string that the software application 115, 125 wishes to present on the display 104. It will be appreciated that the SendEvent and SendDisplayText API calls have been described purely by way of example, and that the same or similar functionality could be achieved with API calls having different parameters or syntax.

The APIs 116, 126 may provide additional API calls to allow a software application 115, 125 to request that the second computer 110 performs particular actions, including: providing keyboard focus to the software application 115, 125; maximising and/or minimising the window in which the graphical user interface of the software application 115, 125 is rendered; displaying the window in which the graphical user interface of the software application 115, 125 is rendered at a particular screen position; displaying the window in which the graphical user interface of the software application 115, 125 is rendered in front of any other windows; and/or displaying the window in which the graphical user interface of the software application 115, 125 is rendered on a particular display 104, for use when multiple displays 104 are connected to the second computer 110.

The rendering control program 117 is responsible for integrating the first computer 120 with the second computer 110 and any further computers, such as the third computer 130. More specifically, the rendering control program 117 integrates the graphical user interfaces and functionality of software applications 115, 125 being executed by the first computer 120, second computer 110 and/or further computers 130. The rendering control program 117 integrates the graphical user interfaces of the software applications 115, 125 by rendering them within a graphical user interface displayed on the second computer 110. The rendering control program 117 integrates the functionality of the software applications 115, 125 by controlling the way in which their graphical user interfaces are rendered on the second computer 110 in response to the occurrence of events within the software applications. The operation of the rendering control program 117 is discussed in greater detail below, with reference to FIG. 5.

In one example, the rendering control program 117 is a stand-alone executable program. In this example, the rendering control program 117 communicates with the window system 111 of the second computer 110 in order to control the rendering of the graphical user interfaces of the software applications 115, 125. However, the functionality of the rendering control program 117 could be integrated into the window system 111 itself, or could be integrated into the operating system of the second computer 110.

The configuration information 118 comprises information for configuring the rendering control program 117. For example, the configuration information 118 may comprise a unique identifier, such as an IP address, for each computer 120, 130 that can be integrated with the second computer 110. The unique identifier allows the rendering control program 117 to identify the computer on which a particular event occurred, which assists the rendering control program 117 in identifying an action to be performed in response to the event. The configuration information 118 may also comprise information for defining the initial appearance of the graphical user interfaces of each application 115, 125 when they are rendered within the graphical user interface of the second computer 110. For example, the configuration information 118 may specify the geometry of a respective window in which each of the graphical user interfaces of each application 115, 125 is displayed. More specifically, the configuration information may specify the height and width of each window, plus the position at which each window is displayed. The configuration information 118 may also specify an initial order of those windows along the z-axis (commonly known as the "z-order"), which allows the window system 111 to determine which windows should be shown and which windows should be hidden if two or more windows overlap. The configuration information 118 may also comprise authentication information for each computer 120, 130 that can be integrated with the second computer 110. For example, the configuration information may comprise a username and/or a password for the first computer 120 and any further computers 130. The authentication information can be used by the second computer 110 to establish a remote presentation protocol session with the other computers 120, 130.

The event table 119 comprises information that defines one or more actions to be performed by the rendering control program 117 in response to the occurrence of particular events in the software applications 115, 125. Each action modifies the behaviour and/or appearance of the graphical user interface in which the respective event occurs. The event table 119 associates a plurality of events with one or more respective actions, thus defining a sequence of actions.

By way of explanation, many computing tasks involving the use of several different software applications require the user to switch between software applications at predictable points during the execution of those software applications. Furthermore, different software applications tend to be used in a predictable sequence. Thus, the need for a user to switch between different software applications (and to switch between different computers, if the software applications are executed by different computers) can be avoided by automatically switching between software applications in a predefined sequence at predefined points in their execution. This can be implemented by causing a software application to send an identification of an event to the second computer 110 when a predefined point in its execution is reached second computer. For example, the software application can invoke the SendEvent API call provided by API 126 in order to send an identification of an event at a particular point in its execution. In this example, the programmer of the software application decides which points in the execution of the software application are significant, and invokes SendEvent at the appropriate point. For example, SendEvent may be invoked when the software application has completed a particular processing operation, when a user interacts with the application software in a particular manner or when an error occurs. Upon receiving the identification of the event, the second computer 110 performs one or more actions that cause the different software applications to be used in a predefined sequence. Thus, a complex computing task can be more easily carried out by performing an action selected from a predefined sequence of actions in response to the occurrence of predefined events in a software application. The event table 119 associates each event with one or more actions, so as to effect the use of the software applications in the desired sequence.

An example of an event table will now be described with reference to FIGS. 2, 3 and 4.

Figure 2:
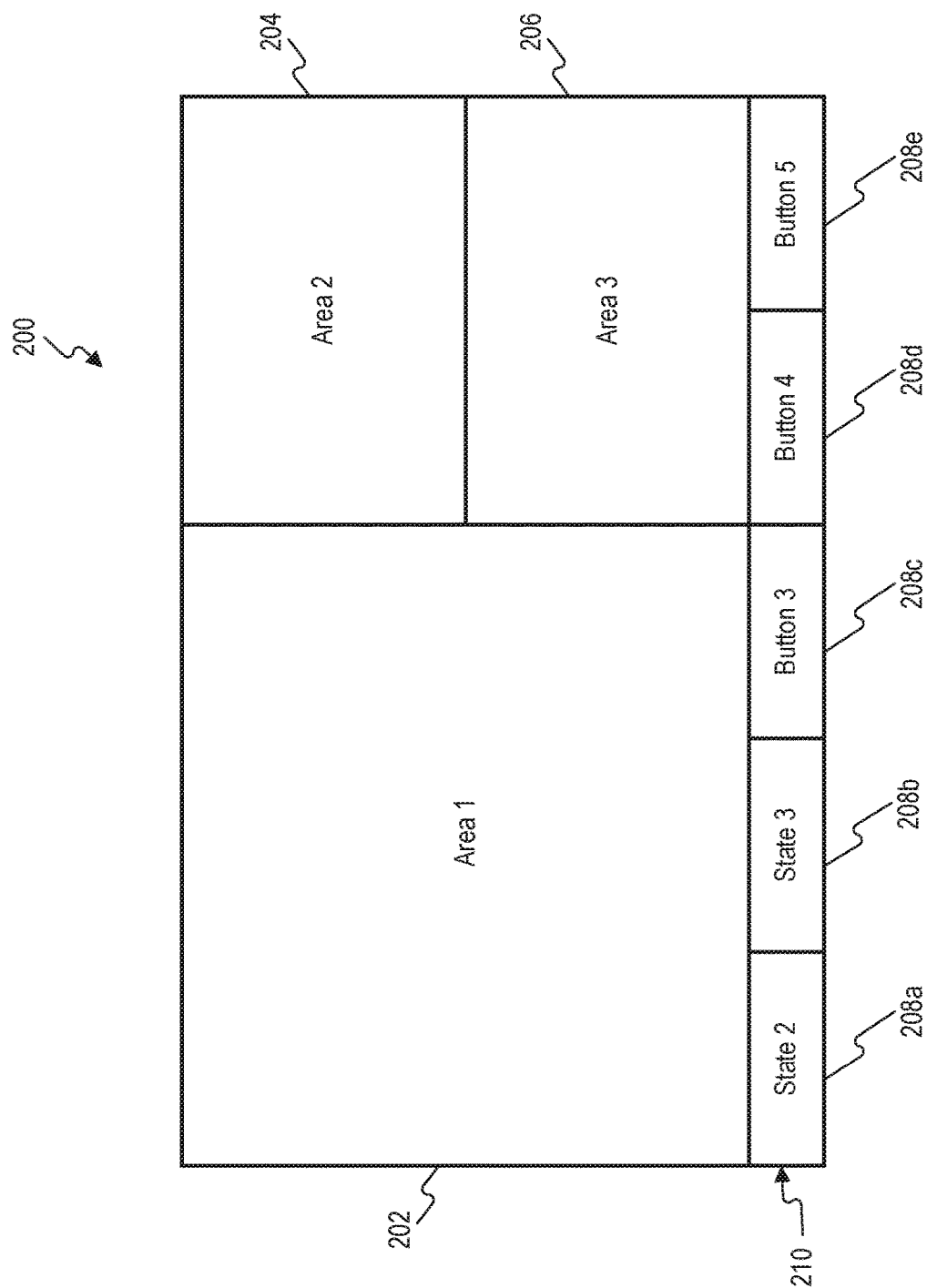
FIG. 2 is an example of a screen generated by integrating a plurality of computers.

FIG. 2 is an example of a screen 200 generated by integrating a plurality of computers in accordance with the present disclosure. The screen 200 is displayed by the second computer 110, on the display device 104. The screen 200 comprises a plurality of areas 202, 204, 206. Three areas 202, 204, 206 are illustrated in FIG. 2, but the screen 200 can comprise more or fewer areas. The screen 200 further comprises a toolbar 210. The toolbar 210 comprises one or more buttons 208. Five buttons 208a, 208b, 208c, 208d, 208e are illustrated in FIG. 2, but the toolbar 210 can comprise more or fewer buttons. The graphical user interface of a software application 115, 125, 135, 145 can be rendered in any of the areas 202, 204, 206.

FIG. 3 is an example of an event table 119. In this example, the event table comprises four columns: a "Current State" column, which identifies each of a plurality of states in which the second computer 110 can exist; a "Received Event" column, which stores information relating to an event that causes the second computer 110 to transition to a different state; an "Action(s)" column, which identifies one or more actions that should be performed in response to receiving an event identified in the "Received Event" column, for a given state of the second computer 110; and a "Next State" column, which identifies the state to which the second computer 110 should transition after performing the actions identified in the "Action(s)" column. The information relating to an event that is stored in the "Received Event" column includes the name of the event (e.g. "Login Successful", "Select State 3"), identification of the application in which the event occurred (e.g. the Source parameter of the SendEvent API call), and identification of the computer in which the event occurred (e.g. a network name or an IP address). It is not necessary for every event that can possibly occur to be associated with an action in the event table 119. For example, in the event table 119 shown in FIG. 3, an action is performed upon receiving a "Warning" event from application 145 on third computer 130 when the second computer 110 is in state 3, but no action is defined if the same event is received when the second computer 110 is in state 2. A received event can be ignored if it has no associated action in the event table 119 or, alternatively, a default action can be performed upon receiving such an event.

FIG. 4 shows the sequence of screens that is generated by the event table 119 shown in FIG. 3. Each screen 200 has the form previously discussed in connection with FIG. 2.

In an initial state (state 0), the rendering control program 117 obtains the initial screen configuration from the configuration information 118. The configuration information causes the rendering control program 117 to render the graphical user interface of software application 135 in area 202, the graphical user interface of software application 115 in area 204, and the graphical user interface of software application 145 in area 206, which results in screen configuration 200a. The second computer 110 then transitions to state 1. In state 1, a "Login Successful" event is received by the second computer 110 from software application 135. Upon receiving this event, the rendering control program 117 consults the event table 119. From the third row of the event table 119, the rendering control program 117 identifies that, when the second computer 110 is in state 1 and a "Login Successful" event is received, two actions should be performed: first, rendering the graphical user interface of software application 135 should be terminated; and second, the graphical user interface of software application 125 should be rendered in area 202. The third row of the event table 119 also indicates that next state of the second computer is state 2. Accordingly, the rendering control program 117 terminates rendering the graphical user interface of software application 135 and causes the graphical user interface of software application 125 to be rendered in area 202, which results in screen configuration 200b. The second computer 110 then transitions to state 2. In state 2, there are two possible events that cause the rendering control program 117 to perform an action. First, in accordance with the fourth row of the event table 119, receiving a "Select State 3" event from application 125 causes the rendering control program 117 to change the positions at which the graphical user interfaces of applications 115 and 125 are rendered. More specifically, the rendering control program 117 renders the graphical user interface of application 115 in Area 202, and renders the graphical user interface of application 125 in area 204, which results in screen configuration 200c. The graphical user interface of application 145 is not affected by these actions, so continues to be rendered in area 206. The second computer 110 then transitions to state 3. Second, in accordance with the fifth row of the event table 119, receiving a "Terminate" event from application 125 causes the rendering control program 117 to terminate rendering the graphical user interfaces of all applications 125, 115, 145. State 3 is generally similar to state 2, so need not be explained in detail.

Returning to FIG. 2, the buttons 208 can be activated by a user in order to force the second computer 110 into a particular state. For example, if a user activates button 208a, the rendering control program 117 causes the second computer 110 to transition to state 2, which causes screen configuration 200b to be displayed. Similarly, if a user activates button 208b, the rendering control program 117 causes the second computer 110 to transition to state 3, which causes screen configuration 200c to be displayed. The buttons allow a predetermined screen configuration to be displayed on demand, without relying upon the occurrence of events that would otherwise be required to cause the second computer 110 to transition to the state associated with that screen configuration. This can be useful if a user wishes to perform a computing task that is not accommodated by the predefined sequence of actions defined in the event table 119, or to return the second computer 110 and the screen 200 to a known state after the occurrence of an error.

The event table 119 may be implemented in any suitable manner, such as in an Extensible Markup Language (XML) document. The term "event table" does not imply that the information contained in the event table 119 must be stored in a tabular form.

Figure 5:
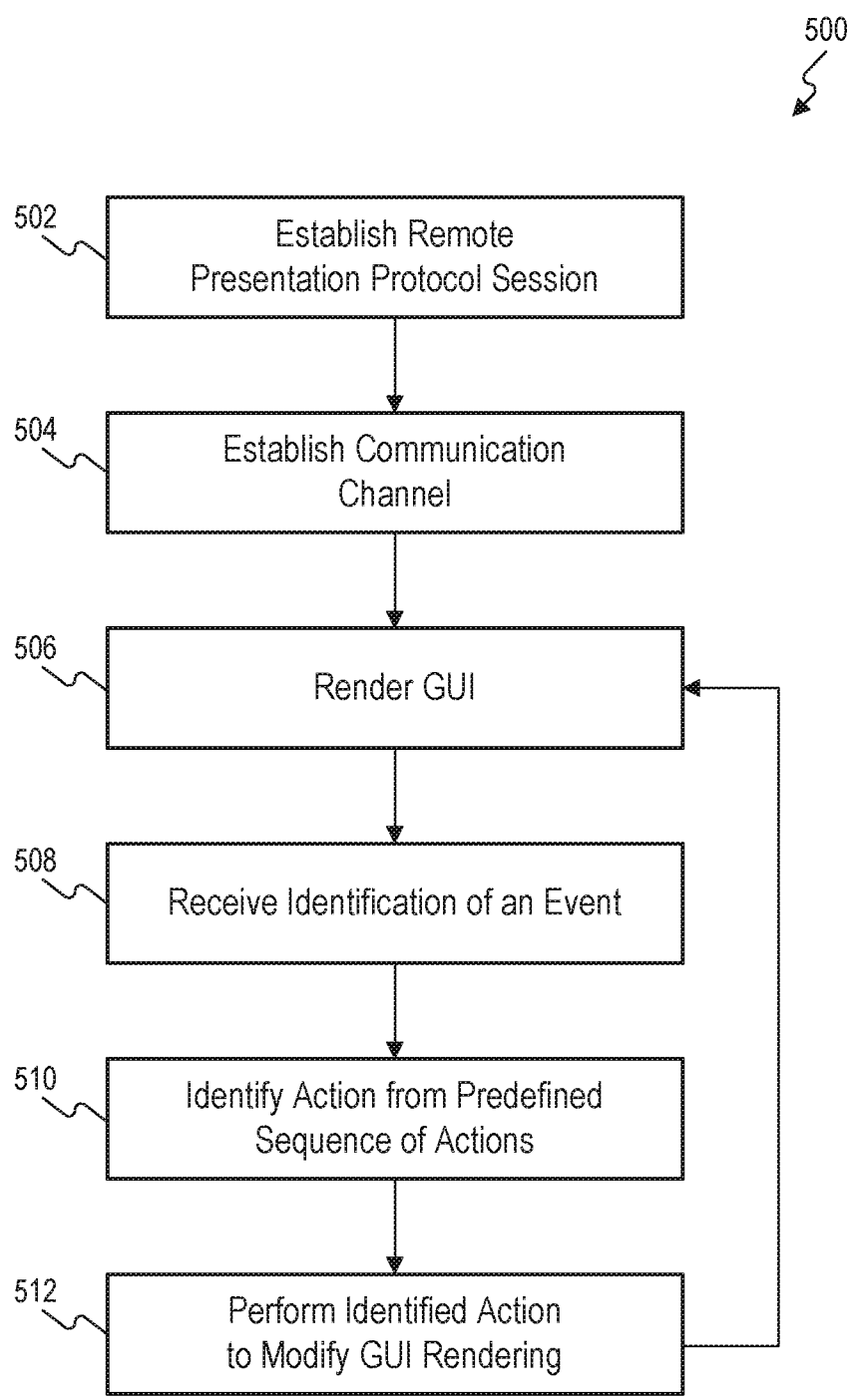
FIG. 5 is a flow diagram of a method of integrating a plurality of computers.

A method 500 of integrating a plurality of computers is shown in FIG. 5. The method 500 will now be described in the context of the computer system 100 illustrated in FIG. 1. In this context, method 500 can be performed by the rendering control program 117 of the second computer 110. In step 502, a remote presentation protocol session is established between the first computer 120 and the second computer 110. The remote presentation protocol session is established using the remote presentation programs 113, 123. The remote presentation protocol session is used to communicate information pertaining to the graphical user interface of the software application 125 between the first computer 120 and the second computer 110 via the network 106. If desired, further remote presentation protocol sessions may also be established between the second computer 110 and the third computer 130, and between the second computer 110 and any additional computers (not shown in FIG. 1).

In step 504, a communication channel is established between the first computer 120 and the second computer 110. The communication channel is established using the communication channel components 114, 124. The first computer 120 uses the communication channel to provide an identification of an event to the second computer 110 via the network 106. For example, the first computer 120 may invoke the SendEvent API call provided by API 126 to send a message describing the event to the second computer 110 using the communication channel. If desired, further communication channels may also be established between the second computer 110 and the third computer 130, and between the second computer 110 and any additional computers (not shown in FIG. 1).

In step 506, the second computer 110 renders the graphical user interface of the software application 125. The term "rendering a graphical user interface" as used herein includes presenting the visual output of a program on a display device, and providing an input received from an input device to the program. Thus, the second computer 110 renders the graphical user interface of the software application 125 by presenting its visual output on the display device 104, and by providing user inputs received from the keyboard 102a and/or the mouse 102b to the software application 125. The graphical user interface of the software application 125 is rendered using the remote presentation programs 123, 113. The remote presentation programs 113, 123 in turn use the window systems 111, 121 to present the visual output of the software application 125 on the display 104 and to provide inputs received from the input devices 102 to the software application 125. If desired, the second computer 110 can simultaneously render the graphical user interfaces of one or more further software applications. Such further software applications may be executed by the first computer 120 or the third computer 130, in which case the remote presentation programs 113, 123 are used to render the graphical user interfaces. Alternatively or additionally, the further software applications may be executed by the second computer 110, such as the software application 115. The graphical user interfaces of any software applications being executed by the second computer 110 are rendered using the window system 111, without the need to use the remote presentation program 113.

Now assume that an event occurs in the software application 125. The occurrence of an event causes the first computer 120 to provide an identification of the event to the second computer 110 in the manner previously described.

In step 508, the second computer 110 receives the identification of the event that has occurred in the software application 125. The identification of the event is received from the first computer 120, via the network 106, using the communication channel established at step 504.

In step 510, the second computer 110 identifies one or more actions to be performed in response to the occurrence of the event in the software application 125. The one or more actions are identified from a predefined sequence of actions stored in the event table 119. In one embodiment, the current state of the second computer 110 is identified, and then the event table 119 is consulted to determine whether an action is associated with the current state and the event that has occurred. The current state of the second computer 110 can be stored by the rendering control program 117. For example, the rendering control program 117 can record the current state of the second computer 110 as the value of a variable. The rendering control program 117 can then identify the current state of the computer 110 by retrieving the value of the variable. If an action is associated with the current state and the event that has occurred, the method proceeds to step 512. If no action is associated with the current state and the event that has occurred, the method returns to step 506 and the second computer 110 renders the graphical user interface of the software application 125 until an identification of another event is received.

In step 512, the second computer 110 performs the one or more actions identified at step 510. Performing an action modifies the way in which the graphical user interface of the software application 125 is rendered by the second computer 110. More specifically, performing an action can cause the second computer 110 to modify the behaviour and/or appearance of the graphical user interface. For example, the behaviour of the graphical user interface can be modified by granting focus of an input device 102, such as keyboard 102a, to the graphical user interface. The appearance of the graphical user interface can be modified by changing the position at which it is displayed on the display device 104, for example by moving a window containing the graphical user interface. Alternatively or additionally, the appearance of the graphical user interface can be modified by changing the size at which it is displayed on the display device 104, for example by maximising, minimising or resizing a window containing the graphical user interface. An action may also cause the second computer 110 to terminate rendering the graphical user interface. After performing the one or more actions, the rendering control program 117 can store a new value in the variable that records the current state of the second computer 110, so as to reflect that the actions have caused the second computer to transition to a new state.

Upon completion of step 512, the method returns to step 506 and the second computer 110 renders the graphical user interface of the software application 125 until an identification of another event is received.

As mentioned above, the second computer 110 can render the graphical user interface of the software application 125 whilst also rendering the user interfaces of one or more further software applications, which can be executed by any of the first, second or third computers 120, 110, 130. An event may also occur in any of the further software applications, causing the further software application to provide an identification of the event to the second computer 110. The second computer 110 can receive an identification of an event that has occurred in any of the further software applications, in the manner described above in connection with step 508. The second computer 110 then identifies one or more actions to be performed in response to the occurrence of the event in the further software application, in the manner described above in connection with step 510. The second computer 110 then performs the identified one or more actions, which can cause the rendering of the user interface of the software application 125 and/or any of the user interfaces of the further applications to be modified in a similar manner to that described above in connection with step 512.

Those skilled in the art will appreciate that there is a wide range of practical situations in which it would be useful to integrate a plurality of computers using the method 500 described above. Purely by way of a non-limiting example, the use of the method to integrate computers in a radiotherapy system will now be described.

As is known to those skilled in the art, radiotherapy is a technique for killing cancerous cells with ionising radiation. The ionising radiation is generated by a device such as a linear accelerator. An example radiotherapy system comprises three computers 110, 120, 130, as illustrated in FIG. 1. The second computer 110 is used by a technician or surgeon who conducts a radiotherapy session. The software application 115 executed by the second computer 110 is a video streaming application, that displays a video signal received from one or more video cameras located in a treatment room that houses the linear accelerator. The technician or surgeon uses the video streaming application to monitor the treatment room in the interests of safety. The first computer 120 is connected to the linear accelerator (not shown in FIG. 1). The software application 125 executed by the first computer 120 is a treatment control program, which controls the linear accelerator. For example, the treatment control program may allow the technician or surgeon to set the parameters to be used during a radiotherapy session, such as the dose of radiation that is to be applied to the patient. The software application 125 may be the Integrity™ treatment control system produced by Elekta AB. The software application 135 executed by the third computer 130 is an oncology information program, which provides information relating to a patient. For example, the oncology information program may be configured to display medical images (such as computed tomography images) of a patient, such that the technician or surgeon can view a tumour and determine how best to treat it. The software application 135 may be the Mosaiq™ oncology information system produced by Elekta AB.

With reference to FIG. 2, a radiotherapy session begins with the graphical user interface of the oncology information program being rendered in area 202, the graphical user interface of the treatment control program being rendered in area 204, and the graphical user interface of the video streaming application being rendered in area 206. This screen configuration grants the largest portion of the screen to the oncology information program, in order that the technician or surgeon can more easily view the tumour to be treated. This screen configuration also ensures that the treatment control program remains visible at all times, which is required for safety and regulatory purposes. When the technician or surgeon has finished viewing the tumour and is ready to start treatment, the user activates a button on the toolbar 210 or selects a menu option in either the oncology information program or the treatment control program. Activating the button or selecting the menu option generates an event, which causes the rendering control program 117 to perform actions that change the configuration of the screen 200. More specifically, the rendering control program resizes and repositions the graphical user interfaces of the oncology information program and treatment control program, such that the graphical user interface of the oncology information program is rendered in area 204, and the graphical user interface of the treatment control program is rendered in area 202. This screen configuration grants the largest portion of the screen to the treatment control program, in order that the technician or surgeon can more easily view the status of the linear accelerator during treatment.

The method disclosed herein can be performed by instructions stored on a processor-readable medium. The processor-readable medium may be: a read-only memory (including a PROM, EPROM or EEPROM); random access memory; a flash memory; an electrical, electromagnetic or optical signal; a magnetic, optical or magneto-optical storage medium; one or more registers of a processor; or any other type of processor-readable medium. In alternative embodiments, the present disclosure can be implemented as control logic in hardware, firmware, software or any combination thereof. The apparatus may be implemented by dedicated hardware, such as one or more application-specific integrated circuits (ASICs) or appropriately connected discrete logic gates. A suitable hardware description language can be used to implement the method described herein with dedicated hardware.

It will be understood that the present disclosure has been described above purely by way of example, and that modifications of detail can be made within the scope of the disclosure.

What is claimed is:

1. A method of controlling a device for generating radiation, for use in a radiotherapy system comprising a first computer and a second computer, the first computer executing a treatment control program for controlling the device for generating radiation, the treatment control program having a first graphical user interface, the method being performed at the second computer and comprising:
   rendering the first graphical user interface, in a screen displayed on a display device, such that the treatment control program remains visible during a radiotherapy session, wherein the screen includes one or more display areas;
   receiving an identification of an event that has occurred in the treatment control program;
   identifying an action to be performed by the second computer in response to the occurrence of the event, wherein the action is identified from a predefined sequence of actions; and
   performing the identified action to modify the rendering of the first graphical user interface so that the treatment control program is displayed on a largest of the one or more display areas of the screen.

2. The method in accordance with claim 1, wherein identifying an action comprises:
   identifying a current state of the second computer; and
   consulting a look-up table to identify a predefined action associated with the current state of the second computer and the event that has occurred.

3. The method in accordance with claim 1, further comprising:
   establishing, by a remote presentation program executed by the second computer, a remote presentation protocol session between the first computer and the second computer; and
   using the remote presentation protocol session to communicate information pertaining to the first graphical user interface between the first computer and second computer via a network,
   wherein the first graphical user interface is rendered using the remote presentation program.

4. The method in accordance with claim 3, wherein the method further comprises:

establishing a communication channel between the first computer and the second computer, the communication channel being distinct from the remote presentation protocol session, wherein the identification of an event is received at the second computer via the communication channel.

5. The method in accordance with claim 1, wherein the second computer executes a second software application having a second graphical user interface, the method further comprising:

rendering the first graphical user interface and the second graphical user interface simultaneously by the second computer.

6. The method in accordance with claim 5, wherein performing the identified action further causes the second computer to modify the rendering of the second graphical user interface.

7. The method in accordance with claim 5, further comprising:

receiving an identification of a second event, the second event having occurred in the second software application;

identifying a second action to be performed by the second computer in response to the occurrence of the second event, wherein the second action is identified from the predefined sequence of actions; and performing the identified second action to modify the rendering of at least one of the first graphical user interface or the second graphical user interface.

8. The method in accordance with claim 7, further comprising integrating a third computer with the first and second computers, the third computer executing a third software application having a third graphical user interface, by rendering the first graphical user interface and the third graphical user interface simultaneously by the second computer.

9. The method in accordance with claim 8, wherein performing the identified action further causes the second computer to modify the rendering of the third graphical user interface.

10. The method in accordance with claim 8, further comprising:

receiving an identification of a third event, the third event having occurred in the third software application;

identifying a third action to be performed by the second computer in response to the occurrence of the third event, wherein the third action is identified from the predefined sequence of actions; and performing the identified third action to modify the rendering of at least one of the first graphical user interface or the third graphical user interface.

11. The method in accordance with claim 10, wherein performing one of said identified actions to modify the rendering of any of the first, second or third graphical user interfaces includes causing the second computer to modify at least one of the behavior or appearance of that graphical user interface.

12. The method in accordance with claim 10, wherein performing one of said identified actions causes the second computer to perform any one or more of:

changing the position at which any of the first, second or third graphical user interfaces is displayed;

changing the size at which any of the first, second or third graphical user interfaces is displayed;

terminating rendering the second or third graphical user interface; or granting focus of an input device to any of the first, second or third graphical user interfaces, wherein the input device is communicatively coupled to the second computer.

13. The method in accordance with claim 1, further comprising:

generating a message at the first computer, the message identifying the event that has occurred in the treatment control program; and transmitting the message, by the first computer, to the second computer.

14. A non-transitory computer-readable medium comprising instructions that, when executed by at least one processor, cause the at least one processor to perform a method of controlling a device for generating radiation, for use in a radiotherapy system comprising a first computer and a second computer, the first computer executing a treatment control program for controlling the device for generating radiation, the treatment control program having a first graphical user interface, the method being performed at the second computer and comprising:

rendering the first graphical user interface in a screen displayed on a display device, such that the treatment control program remains visible during a radiotherapy session, wherein the screen includes one or more display areas;

receiving an identification of an event that has occurred in the treatment control program;

identifying an action to be performed by the second computer in response to the occurrence of the event, wherein the action is identified from a predefined sequence of actions; and performing the identified action to modify the rendering of the first graphical user interface so that the treatment control program is displayed on a largest of the one or more display areas of the screen.

15. A non-transitory computer readable medium in accordance with claim 14, wherein identifying an action comprises:

identifying a current state of the second computer; and consulting a look-up table to identify a predefined action associated with the current state of the second computer and the event that has occurred.

16. A radiotherapy system comprising:

a first computer connected to a device for generating radiation, the first computer further including a treatment control program for controlling the device for generating radiation, the treatment control program having a graphical user interface; and a second computer operable to communicate with the first computer, wherein the second computer is configured to:

establish a remote presentation protocol session between the first computer and the second computer;

establish a communication channel between the first computer and the second computer, the communication channel being distinct from the remote presentation protocol session;

render the graphical user interface, based on information communicated via the remote presentation protocol session, in a screen displayed on a display device, such that the treatment control program remains visible during a radiotherapy session, wherein the screen includes one or more display areas;

receive, at the second computer via the communication channel, an identification of an event that has occurred in the treatment control program;

identify an action to be performed by the second computer in response to the occurrence of the event, wherein the action is identified from a predefined sequence of actions; and perform the identified action to modify the rendering of the graphical user interface so that the treatment control program is displayed on a largest of the one or more display areas of the screen.

17. A radiotherapy system in accordance with claim 16, wherein the second computer is further operable to communicate with a third computer, the third computer including an oncology information program for providing information relating to a patient to be treated by the radiotherapy system.

18. A radiotherapy system in accordance with claim 16, wherein the second computer executes a video streaming application that displays video signals received from one or more video cameras located in a room housing the device for generating radiation.

19. A radiotherapy system in accordance with claim 16, wherein the identified action to modify the rendering of the graphical user interface comprises causing the second computer to modify at least one of the behavior or appearance of the graphical user interface.

20. A radiotherapy system in accordance with claim 16, wherein identifying an action comprises:

identifying a current state of the second computer; and consulting a look-up table to identify a predefined action associated with the current state of the second computer and the event that has occurred.

\* \* \* \* \*